United States Patent
Kister et al.

(10) Patent No.: US 11,363,816 B2
(45) Date of Patent: Jun. 21, 2022

(54) 4-AMINO-6-(HETEROCYCLIC)PICOLINATES AND 6-AMINO-2-(HETEROCYCLIC)PYRAMIDINE-4-CARBOXYLATES AND THEIR USE AS HERBICIDES

(71) Applicant: Dow AgroSciences LLC, Indianapolis, IN (US)

(72) Inventors: Jeremy Kister, Carmel, IN (US); Norbert M Satchivi, Carmel, IN (US); Jeffrey M Epp, Noblesville, IN (US); Joshua Roth, Carmel, IN (US)

(73) Assignee: Corteva Agriscience LLC, Indianapolis, IN (US)

( * ) Notice: Subject to any disclaimer, the term of this patent is extended or adjusted under 35 U.S.C. 154(b) by 0 days.

(21) Appl. No.: 16/612,368

(22) PCT Filed: May 4, 2018

(86) PCT No.: PCT/US2018/031004
§ 371 (c)(1),
(2) Date: Nov. 8, 2019

(87) PCT Pub. No.: WO2018/208582
PCT Pub. Date: Nov. 15, 2018

(65) Prior Publication Data
US 2020/0068888 A1    Mar. 5, 2020

Related U.S. Application Data

(60) Provisional application No. 62/504,148, filed on May 10, 2017.

(51) Int. Cl.
*A01N 43/40* (2006.01)
*C07D 401/10* (2006.01)

(52) U.S. Cl.
CPC .......... *A01N 43/40* (2013.01); *C07D 401/10* (2013.01)

(58) Field of Classification Search
CPC ............... A01N 43/40; C07D 401/10
See application file for complete search history.

(56) References Cited

U.S. PATENT DOCUMENTS

| 4,044,140 | A | 8/1977 | Sherlock |
| 4,877,897 | A | 10/1989 | Swithenbank et al. |
| 9,611,282 | B2 * | 4/2017 | Eckelbarger ........... A01N 43/78 |
| 2003/0114311 | A1 | 6/2003 | Balko et al. |
| 2015/0005156 | A1 * | 1/2015 | Dash ................... B01J 37/0036 502/225 |
| 2015/0005165 | A1 | 1/2015 | Hoffman et al. |

OTHER PUBLICATIONS

Dow Agrosciences LLC, Examination Report, dated Aug. 16, 2019, Pakistan Patent Application No. 330/2018 (May 9, 2018).
Dow Agrosciences LLC, International Search Report, dated Sep. 25, 2014, WO 2014/151005, para [0005], [0011], [0016], [0137], [0209], [0231], Table 15; claim 33.
Dow Agrosoences LLC, European Search Report, dated Nov. 25, 2020, European Patent Application No. 18 798 826.6, paragraphs.
Dow Agrosciences LLC, Official Acton, dated Feb. 24, 2021, Eurasian Patent Application No. 201992666 (Dec. 9, 2019).
Dow Agrosciences LLC, Official Action, dated Nov. 23, 2021, Eurasian Patent Application No. 201992666 (Dec. 9, 2019).

\* cited by examiner

*Primary Examiner* — Rei Tsang Shiao

(57) ABSTRACT

4-Amino-6-(heterocyclic)picolinicates and their derivatives; 6-amino-2-(heterocyclic)pyrimidine-4-carboxylates and their derivatives; and methods of using the same as herbicides.

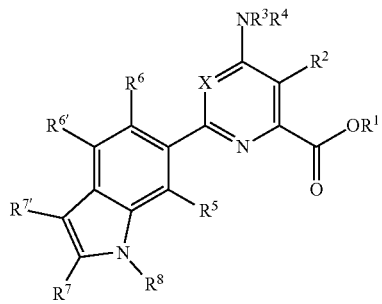

(I)

28 Claims, No Drawings

4-AMINO-6-(HETEROCYCLIC)PICOLINATES AND 6-AMINO-2-(HETEROCYCLIC)PYRAMIDINE-4-CARBOXYLATES AND THEIR USE AS HERBICIDES

CROSS REFERENCE TO RELATED APPLICATIONS

This application is the U.S. national stage entry of International Application No. PCT/US2018/031004, filed May 4, 2018, which claims priority to and any benefit of U.S. Provisional Patent Application Ser. No. 62/504,148 filed May 10, 2017, the entire disclosures of which are hereby expressly incorporated by reference.

FIELD

The present disclosure includes herbicidal compounds, compositions containing the same, and methods of controlling undesirable vegetation with such compounds and compositions.

BACKGROUND

The occurrence of undesirable vegetation, e.g., weeds, is a constant problem facing farmers in crops, pasture, and other settings. Weeds compete with crops and negatively impact crop yield. The use of chemical herbicides is an important tool in controlling undesirable vegetation. The undesirable vegetation *Kochia* and common poppy are particularly problematic in crop fields (e.g., wheat, barley, corn, oats, canola, and sugar beets), pastures, roadsides, wastelands, and ditch banks.

For example, *Kochia* (*Kochia scoparia*) is an early-emerging summer annual species commonly found in the western United States and Canada. It is a herbaceous dicot and member of the Chenopodiaceae family. *Kochia* was introduced into North America from Europe as an ornamental because of its red color in late summer and fall. *Kochia* (*Kochia scoparia* (L.) Schrad.) is one of the most troublesome annual broadleaf weeds in crop fields, pastures, roadsides, wastelands, and ditch banks across the Northern Great Plains (NGP). If not controlled early, *Kochia* causes severe yield reductions (up to 60%) in crops, including wheat, barley, corn, and sugar beet, and can be a major problem weed in chem-fallow.

Seeds have little-to-no dormancy, and the majority (>90%) of the seeds lying on or near the soil surface in a no-till condition germinate early in the spring, with two to three emergence flushes through the summer. *Kochia* exhibits rapid growth and flowers in late summer. The weed is capable of self- and cross-pollination, and reproduces by seed. A single *Kochia* plant is capable of producing up to 50,000 seeds that can spread by wind, water, contaminants in hay, agricultural equipment, or by on-farm vehicles. At maturity, the plant breaks off at the base of the stem and "tumbles" across the landscape with the prevailing wind, a unique and rapid mechanism of seed dispersal. Furthermore, *Kochia* is well adapted to drought, salt, heat, and cold conditions.

Herbicides that have been used in an attempt to control *Kochia* include acetolactate synthase (ALS)-inhibiting herbicides, fluroxypyr, dicamba, and glyphosate. Fluroxypyr and dicamba are selective herbicides that can control broadleaf weeds and typically not injure grasses. (2-Dichlorophenoxy)acetic acid (2,4-D), which is often applied for *Kochia* control, is not effective.

Glyphosate (such as Roundup®, a registered mark of Monsanto Technology LLC, a Delaware Limited Liability Company, or other similar generics) is a non-selective, broad-spectrum herbicide used for weed control. However, various factors concerning the use of glyphosate for more than a decade for burndown weed control prior to planting, in chem-fallow, and for in-crop applications in Roundup Ready® (also a registered mark of Monsanto Technology LLC) crops, have resulted in the evolution of glyphosate-resistant weeds (presently 24 species in the United States), including *Kochia*. For example, *Kochia* biotypes resistant to triazines, auxins, ALS herbicides, and glyphosate have been well documented.

Corn poppy or common poppy (*Papaver rhoeas*) is one of the most problematic dicot weed in winter cereals in areas of southern Europe that have a Mediterranean climate. Corn poppy is a competitive weed that is well known for its ability to reduce cereal yield. The ability of this species to invade, grow, and persist in cereal fields can be attributed to the formation of a persistent seed bank, an extended period of germination, and high seed production. Management of poppy has become a serious and increasing challenge for cereal growers and authorities in Europe due to the spreading of herbicide-resistant biotypes of poppy. Populations of *P. rhoeas* resistant to sulfonylurea herbicides or/and auxinic herbicides have been reported in Belgium, Denmark, France, Germany, Greece, Italy, Spain, Sweden and the United Kingdom. Some populations of *P. rhoeas* resistant to photosystem II (PSII)-inhibiting herbicides have been found in Poland. The spreading of herbicide-resistant biotypes of *P. rhoeas* is a threat to the profitability of cereal production systems.

Thus, there remains a need for new chemical herbicides that offer a broader spectrum of weed control, selectivity, minimal crop damage, storage stability, ease of handling, higher activity against weeds, and/or a means to address herbicide-tolerance developed with respect to conventional herbicides.

SUMMARY

Provided herein are compounds of Formula (I):

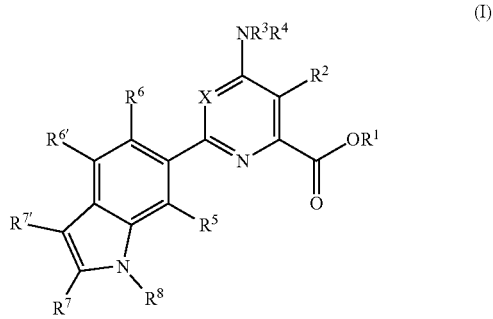

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio, or $C_1$-$C_3$ haloalkylthio;

$R^1$ is $C_3$-$C_{12}$ alkynyl or $C_1$-$C_3$ alkyl substituted with CN;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^5$ is hydrogen, halogen, $C_1$-$C_4$ alkyl, $C_1$-$C_4$ haloalkyl, cycloalkyl, halocycloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_6$ alkylcarbonyl, $C_1$-$C_6$ cycloalkylcarbonyl, $C_1$-$C_6$ haloalkylcarbonyl, $C_1$-$C_6$ alkoxycarbonyl, $C_1$-$C_6$ haloalkoxycarbonyl, arylcarbonyl, heteroarylcarbonyl, $C_1$-$C_6$ alkylcarbamyl, $C_1$-$C_6$ alkylthio, $C_1$-$C_6$ alkylsulfonyl, $C_1$-$C_6$ haloalkylsulfonyl, arylsulfonyl, $C_1$-$C_6$ trialkylsilyl, amino, $C_1$-$C_4$ alkylamino, cyano, or phenyl, or an N-oxide thereof.

Also provided are methods of controlling undesirable vegetation including providing the compound of Formula (I) and (a) contacting the undesirable vegetation or area adjacent to the undesirable vegetation or (b) pre-emergently contacting soil or water a herbicidally effective amount of at least one compound of Formula (I) or agriculturally acceptable derivative thereof.

DETAILED DESCRIPTION

I. Definitions

As used herein, herbicide and herbicidal active ingredient may be understood to include a compound that controls undesirable vegetation when applied in an appropriate amount.

As used herein, control of or controlling undesirable vegetation means killing or preventing the vegetation, or causing some other adverse modifying effect to the vegetation e.g., deviations from natural growth or development, regulation, desiccation, retardation, and the like.

As used herein, a herbicidally effective or vegetation controlling amount may be understood to include an amount of herbicidal active ingredient the application of which controls the relevant undesirable vegetation.

As used herein, applying a herbicide or herbicidal composition may be understood to include delivering it directly to the targeted vegetation or to the locus thereof or to the area where control of undesired vegetation is desired. Exemplary methods of application include, but are not limited to, pre-emergently contacting soil or water, post-emergently contacting the undesirable vegetation or area adjacent to the undesirable vegetation.

As used herein, plants and vegetation may include, but are not limited to, dormant seeds, germinant seeds, emerging seedlings, plants emerging from vegetative propagules, immature vegetation, and established vegetation.

As used herein, immature vegetation may be understood to include small vegetative plants prior to reproductive stage, and mature vegetation refers to vegetative plants during and after reproductive stage.

As used herein, unless otherwise specified, acyl refers to formyl, $C_1$-$C_3$ alkylcarbonyl, and $C_1$-$C_3$ haloalkylcarbonyl. $C_1$-$C_6$ acyl refers to formyl, $C_1$-$C_5$ alkylcarbonyl, and $C_1$-$C_5$ haloalkylcarbonyl (the group contains a total of 1 to 6 carbon atoms).

As used herein, alkyl refers to saturated, straight-chained or branched saturated hydrocarbon moieties. Unless otherwise specified, $C_1$-$C_{10}$ alkyl groups are intended. Examples include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl.

As used herein, haloalkyl refers to straight-chained or branched alkyl groups, where in these groups the hydrogen atoms may be substituted partially or entirely with halogen atoms. Unless otherwise specified, $C_1$-$C_8$ groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl.

As used herein, alkenyl refers to unsaturated, straight-chained, or branched hydrocarbon moieties containing a double bond. Unless otherwise specified, $C_2$-$C_8$ alkenyl are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. Vinyl refers to a group having the structure —CH=CH$_2$; 1-propenyl refers to a group with the structure -CH=CH—CH$_3$; and 2-propenyl refers to a group with the structure —CH$_2$—CH=CH$_2$.

As used herein, alkynyl represents straight-chained or branched hydrocarbon moieties containing a triple bond. Unless otherwise specified, $C_2$-$C_8$ alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl.

As used herein, alkoxy refers to a group of the formula R—O—, where R is alkyl as defined above. Unless otherwise specified, alkoxy groups wherein R is a $C_1$-$C_8$ alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-dimethyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethyl-butoxy, 1,1,2-trimethyl-propoxy, 1,2,2-trimethyl-propoxy, 1-ethyl-1-methyl-propoxy, and 1-ethyl-2-methyl-propoxy.

As used herein, haloalkoxy refers to a group of the formula R—O—, where R is haloalkyl as defined above. Unless otherwise specified, haloalkoxy groups wherein R is a $C_1$—C alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, and 1,1,1-trifluoroprop-2-oxy.

As used herein, alkylthio refers to a group of the formula R—S— where R is alkyl as defined above. Unless otherwise specified, alkylthio groups wherein R is a $C_1$-$C_8$ alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio.

As used herein, haloalkylthio refers to an alkylthio group as defined above wherein the carbon atoms are substituted partially or entirely with halogen atoms. Unless otherwise specified, haloalkylthio groups wherein R is a $C_1$-$C_8$ alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio, and 1,1,1-trifluoroprop-2-ylthio.

As used herein, aryl, as well as derivative terms such as aryloxy, refers to a phenyl, indanyl or naphthyl group with phenyl being preferred. The term heteroaryl, as well as derivative terms such as heteroaryloxy, refers to a 5- or 6-membered aromatic ring containing one or more heteroatoms, viz., N, O or S; these aromatic and heteroaromatic rings may be fused to other aromatic and/or heteroaromatic systems. The aryl or heteroaryl substituents may be unsubstituted or substituted with one or more substituents selected from halogen, hydroxy, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein alkylcarbonyl refers to an alkyl group bonded to a carbonyl group. $C_1$-$C_3$ alkylcarbonyl and $C_1$-$C_3$ haloalkylcarbonyl refer to groups wherein a $C_1$-$C_3$ alkyl group is bonded to a carbonyl group (the group contains a total of 2 to 4 carbon atoms).

As used herein, alkoxycarbonyl refers to a group of the formula

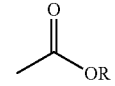

wherein R is alkyl.

As used herein, arylalkyl refers to an alkyl group substituted with an aryl group. $C_7$-$C_{10}$ arylalkyl refers to a group wherein the total number of carbon atoms in the group is 7 to 10.

As used herein alkylamino refers to an amino group substituted with one or two alkyl groups, which may be the same or different.

As used herein haloalkylamino refers to an alkylamino group wherein the alkyl carbon atoms are substituted partially or entirely with halogen atoms.

As used herein, $C_1$-$C_6$ alkylaminocarbonyl refers to a group of the formula RNHC(O)— wherein R is $C_1$-$C_6$ alkyl, and $C_1$-$C_6$ dialkylaminocarbonyl refers to a group of the formula $R_2$NC(O)— wherein each R is independently $C_1$-$C_6$ alkyl.

As used herein alkylcarbamyl refers to a carbamyl group substituted on the nitrogen with an alkyl group.

As used herein alkylsulfonyl refers to a group of the formula

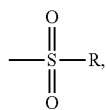

where R is alkyl.

As used herein carbamyl (also referred to as carbamoyl and aminocarbonyl) refers to a group of the formula

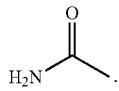

As used herein dialkylphosponyl refers to a group of the formula

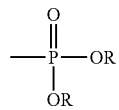

where R is independently alkyl in each occurrence.

As used herein, $C_1$-$C_6$ trialkylsilyl refers to a group of the formula —$SiR_3$ wherein each R is independently a $C_1$-$C_6$ alkyl group (the group contains a total of 3 to 18 carbon atoms).

As used herein Me refers to a methyl group; OMe refers to a methoxy group; i-Pr refers to an isopropyl group.

As used herein, the term halogen including derivative terms such as halo refers to fluorine, chlorine, bromine and iodine.

As used herein, agriculturally acceptable salts and esters refer to salts and esters that exhibit herbicidal activity or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as substituted or unsubstituted alkylhalides, substituted or unsubstituted alkynylhalides, substituted or unsubstituted cyanoalkylhalides (e.g., cyanomethyl acetate, such as cyanomethyl 2-bromoacetate)), or substituted or unsubstituted alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compounds of the Formula (I) include N-oxides. Pyridine N-oxides can be obtained by oxidation of the corresponding pyridines. Suitable oxidation methods are described, for example, in Houben-Weyl, *Methoden der organischen Chemie* [*Methods in organic chemistry*], expanded and subsequent volumes to the 4th edition, volume E 7b, p. 565 f.

II. Compounds

The compounds described herein are compounds of Formula (I):

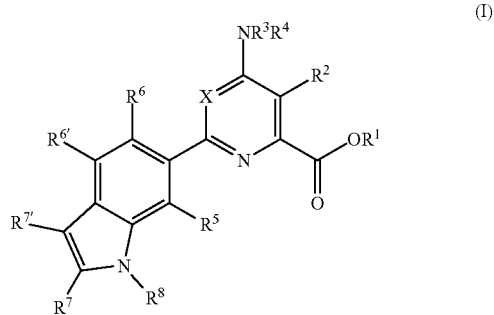

wherein

X is X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio, or $C_1$-$C_3$ haloalkylthio;

$R^1$ is $C_3$-$C_{12}$ alkynyl or $C_1$-$C_3$ alkyl substituted with CN;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_6$ alkylcarbonyl, $C_1$-$C_6$ cycloalkylcarbonyl, $C_1$-$C_6$ haloalkylcarbonyl, $C_1$-$C_6$ alkoxycarbonyl, $C_1$-$C_6$ haloalkoxycarbonyl, arylcarbonyl, heteroarylcarbonyl, $C_1$-$C_6$ alkylcarbamyl, $C_1$-$C_6$ alkylthio, $C_1$-$C_6$ alkylsulfonyl, $C_1$-$C_6$ haloalkylsulfonyl, arylsulfonyl, $C_1$-$C_6$ trialkylsilyl, amino, $C_1$-$C_4$ alkylamino, cyano, or phenyl;

In some embodiments, the compound of Formula (I) is (Ia)

wherein

X is N, CH, CF, CCl, or CBr;

$R^1$ is $C_3$-$C_{12}$ alkynyl or $C_1$-$C_3$ alkyl substituted with CN;

$R^2$ is chlorine;

$R^3$ and $R^4$ are hydrogen;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$ and $R^{6'}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_6$ alkylcarbonyl, $C_1$-$C_6$ cycloalkylcarbonyl, $C_1$-$C_6$-alkoxycarbonyl, or arylcarbonyl;

or an N-oxide or agriculturally acceptable salt thereof.

In some embodiments, the compound of Formula (I) is (Ib)

wherein $R^2$ is halogen, $C_2$-$C_4$-alkenyl, $C_2$-$C_4$ haloalkenyl, or $C_1$-$C_4$ alkoxy;

$R^5$ is hydrogen or F;

$R^6$ is hydrogen or F;

$R^{6'}$ is hydrogen; and $R^7$ and $R^{7'}$ are independently hydrogen or halogen.

In some embodiments, the compound of Formula (I) is (Ic)

wherein $R^2$ is chlorine, methoxy, vinyl, or 1-propenyl;

$R^3$ and $R^4$ are hydrogen; and

X is CF.

In some embodiments:

$R^1$ is propargyl; and the compound of Formula (I) is

In some embodiments:

R$^1$ is cyanomethyl;

the compound of Formula (I) is

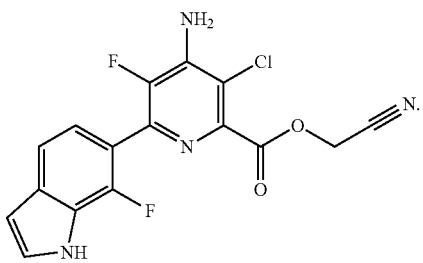 [SMILES: N#CCOC(=O)c1nc(-c2ccc3cc[nH]c3c2F)c(F)c(N)c1Cl]

III. Methods of Preparation

Procedures to synthesize 4-amino-6-(heterocyclic)picolinic acids, wherein X is CH or CF and R$^1$ is H, and 6-amino-2-(heterocyclic)pyrimidine carboxylic acids, wherein X is N and R$^1$ is H are described in U.S. Pat. No. 9,637,505 to Eckelbarger et al., which is incorporated by reference herein in its entirety.

Procedures to synthesize the compounds of Formula (I) wherein R$^1$, R$^2$, R$^3$, R$^4$, R$^5$, R$^6$, R$^{6'}$, R$^7$, R$^{7'}$, and R$^8$ are as defined above is shown in Scheme 1

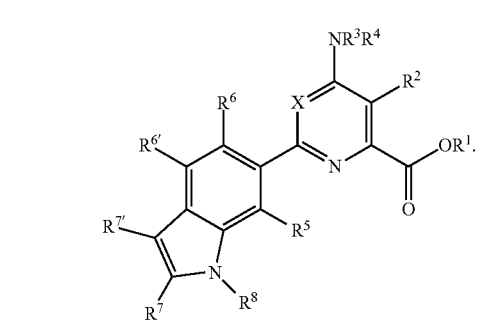

Scheme 1

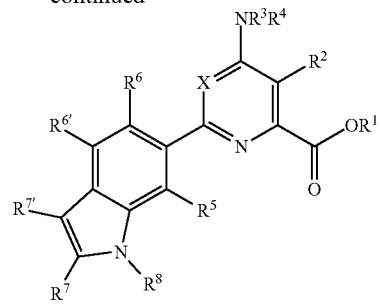

Formula (I)

Acids 1-1 can be converted to compounds of Formula (I) by esterification (Scheme 1, step a). The esters can be prepared by coupling of the acids with an alcohol using any number of suitable activating agents such as those used for peptide couplings including dicyclohexylcarbodiimide (DCC) or carbonyl diimidazole (CDI); by reacting the acids with alkylating agents such as substituted or unsubstituted alkyl halides, substituted or unsubstituted alkynyl halides, substituted or unsubstituted cyanoalkynylhalides, or substituted or unsubstituted alkyl sulfonates in the presence of a base such as triethylamine or lithium or potassium carbonate; by reacting the corresponding acid chloride of an acid with an appropriate alcohol; or by reacting the corresponding acid with an appropriate alcohol in the presence of an acid catalyst. The reactions can be conducted in polar, aprotic solvents such as dimethyl sulfoxide, N,N-dimethylformamide, dichloromethane, or 1,2-dichloroethane.

IV. Mixtures

In some embodiments, the compounds, compositions, and methods provided herein are used in conjunction with one or more other herbicides to control a wider variety of undesirable vegetation. When used in conjunction with other herbicides, the compounds described herein can be formulated with the other herbicide or herbicides, tank-mixed with the other herbicide or herbicides or applied sequentially with the other herbicide or herbicides. Some of the herbicides that can be employed in conjunction with the compounds of the present disclosure include, but are not limited to, 4-CPA; 4-CPB; 4-CPP; 2,4-D; 2,4-D choline salt, 2,4-D esters and amines; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorprocarb, chlorpropham, chlorsulfuron, chlorthal, chlorthiamid, cinidon-ethyl, cinmethylin, cinosulfuron, cisanilide, clacyfos, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyranil, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, florasulam, florpyrauxifen-benzyl, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halosafen, halosulfuron-methyl, haloxydine, haloxyfop-methyl, haloxyfop-P-methyl, halauxifenmethyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lancotrione, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr esters and amines, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate and xylachlor. The mixing partner(s) can be formulated as the free acid or base or as a salt or ester as defined above.

The compounds and compositions described herein can generally be employed in combination with known herbicide safeners, such as benoxacor, benthiocarb, brassinolide, cloquintocet (e.g., mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, 2-dichloromethyl-2-methyl-1,3-dioxolane also know as MG 191, dichloroacetyl-1-oxa-4-azaspiro(4,5)-decane also known as MON 4660, naphthalic anhydride (NA), oxabetrinil, (R,S)-3-dichloroacetyl-2,2,5-trimethyloxazolidine also known as R-29148, metcamifen, N-phenylsulfonylbenzoic acid amides, or mixtures thereof, to enhance their selectivity.

In some embodiments, the compounds provided herein may be employed in mixtures containing a herbicidally effective amount of the compound along with at least one agriculturally acceptable adjuvant or carrier. Exemplary adjuvants or carriers include those that are not phytotoxic or significantly phytotoxic to valuable crops, e.g., at the concentrations employed in applying the compositions for selective weed control in the presence of crops, and/or do not react or significantly react chemically with the compounds provided herein or other composition ingredients. Such mixtures can be designed for application directly to weeds or their locus or can be concentrates or formulations that are diluted with additional carriers and adjuvants before application. They can be solids, such as, for example, dusts, granules, water dispersible granules, or wettable powders, or liquids, such as, and for example, emulsifiable concentrates, solutions, emulsions or suspensions. They can also be provided as a pre-mix or tank-mixed.

Suitable agricultural adjuvants and carriers that are useful in preparing the herbicidal mixtures of the disclosure are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. Exemplary organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethylhexyl stearate, n-butyl oleate, isopropyl myristate, propylene glycol dioleate, di-octyl succinate, di-butyl adipate, di-octyl phthalate and the like; esters of mono-, di- and poly-carboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, and the like. In some embodiments, water is the carrier for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like. Suitable solid carriers may also include combinations of the aforementioned solid carriers.

In some embodiments, one or more surface active agents are utilized in the compositions of the present disclosure. Such surface active agents are, in some embodiments, employed in both solid and liquid compositions, e.g., those designed to be diluted with carrier before application. The surface active agents may be anionic, cationic or nonionic in character and can be employed as emulsifying agents, wetting agents, suspending agents, or for other purposes. Surfactants conventionally used in the art of formulation and which may also be used in the present formulations are described, inter alia, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcoholalkylene-oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl-phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters.

Often times, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this disclosure is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

V. Methods of Application

The present compositions can be applied to weeds or their locus by the use of conventional ground or aerial dusters, sprayers, and granule applicators, by addition to irrigation or flood water, and by other conventional means known to those skilled in the art.

In some embodiments, the present compounds and compositions described herein are applied as a post-emergence application, pre-emergence application, in-water application to flooded paddy rice or water bodies (e.g., ponds, lakes and streams), or burn-down application.

In some embodiments, the compounds and compositions provided herein are utilized to control weeds in crops, including but not limited to citrus, apple, rubber, palm oil, forestry, direct-seeded, water-seeded and transplanted rice, wheat, barley, oats, rye, *Sorghum*, corn/maize, pastures, grasslands, rangelands, fallowland, turf, tree and vine orchards, aquatics, or row-crops, as well as non-crop settings, e.g., industrial vegetation management or rights of way. In some embodiments, the compounds and compositions are used to control woody plants, broadleaf and grass weeds, or sedges.

In some embodiments, the compounds and compositions provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall *Panicum*, PANDI), *Paspalum dilatatum* Poir. (dallisgrass, PASDI), *Cyperus difformis* L. (smallflower flatsedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (*Monochoria*, MOOKA), *Monochoria vaginalis* (Burm. F.) C. Presl ex Kuhth, (*monochoria*, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp *Sesbania*, SEBEX), or *Sphenoclea zeylanica* Gaertn. (gooseweed, SPDZE).

In some embodiments, the compounds and compositions provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POAAN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (*Kochia*, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the compounds and compostions provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly *sida*, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the compounds and compositions provided herein are utilized to control undesirable vegetation found in row crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *Panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly *Sida*, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, application rates of about 1 to about 4,000 grams/hectare (g/ha) are employed in post-emergence operations. In some embodiments, rates of about 1 to about 4,000 g/ha are employed in pre-emergence operations.

The compounds, compositions, and methods described herein be used to control undesirable vegetation on 5-enolpyruvylshikimate-3-phosphate (EPSP) synthase inhibitor-tolerant (e.g., glyphosate-tolerant-), glutamine synthetase inhibitor-tolerant (e.g., glufosinate-tolerant-), synthetic auxin-tolerant (e.g., dicamba-tolerant-, phenoxy auxin-tolerant-, pyridyloxy auxin-tolerant-), auxin transport inhibitor-tolerant, acetyl CoA carboxylase (ACCase) inhibitor-tolerant- (e.g., aryloxyphenoxypropionate-tolerant-), acetolactate synthase (ALS) or acetohydroxy acid synthase (AHAS) inhibitor-tolerant- (e.g., imidazolinone-tolerant-, sulfonylurea-tolerant, pyrimidinylthiobenzoate-tolerant, triazolopyrimidine-tolerant, sulfonylaminocarbonyltriazolinone-tolerant), 4-hydroxyphenyl-pyruvate dioxygenase (HPPD) inhibitor-tolerant-, protoporphyrinogen oxidase (PPO) inhibitor-tolerant-, photosystem (PS) II inhibitor-tolerant (e.g., triazine-tolerant- and bromoxynil-tolerant-) crops (such as, but not limited to, soybean, cotton, canola/oilseed rape, rice, cereals, corn, turf, etc), for example, in conjunction with EPSP synthase inhibitors (e.g., glyphosate), glutamine synthetase inhibitors (e.g., glufosinate), synthetic auxins (e.g., dicamba, phenoxy auxins, pyridyloxy auxins), ACCase inhibitors (e.g., aryloxyphenoxypropionates), ALS inhibitors (e.g., imidazolinones, sulfonylureas, pyrimidinylthiobenzoates, triazolopyrimidines, and sulfonylaminocarbonyltriazolinones), HPPD inhibitors, PPO inhibitors, and PS II inhibitors (e.g., triazines and bromoxynil). The compositions and methods may be used in controlling undesirable vegetation in crops possessing multiple or stacked traits conferring tolerance to multiple chemistries and/or inhibitors of multiple modes of action.

The compounds and compositions provided herein may also be employed to control herbicide resistant or tolerant weeds. Exemplary resistant or tolerant weeds include, but are not limited to, biotypes resistant or tolerant to ALS (or AHAS) inhibitors, PS II inhibitors, ACCase inhibitors, synthetic auxins, PS I inhibitors, EPSP synthase inhibitors, microtubule assembly inhibitors, lipid synthesis inhibitors, PPO inhibitors, carotenoid biosynthesis inhibitors, very long chain fatty acid (VLCFA) inhibitors, phytoene desaturase (PDS) inhibitors, glutamine synthetase inhibitors, HPPD inhibitors, mitosis inhibitors, cellulose biosynthesis inhibitors, herbicides with multiple modes of action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes of action.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1: Preparation of 7-fluoro-1-(triisopropylsilyl)-1H-indole (1)

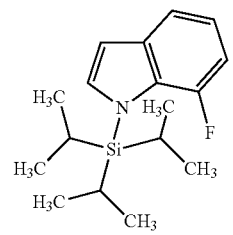 [SMILES: CC(C)[Si](C(C)C)(C(C)C)n1ccc2cccc(F)c21]

The title compound was prepared according to a literature procedure Das, A., et al. *Org. Lett.* 2017, 19, 5794-5797, which is incorporated herein by reference in its entirety.

Example 2: Preparation of 7-fluoro-6-(4,4,5,5-tetramethyl-1,3,2-dioxaborolan-2-yl)-1-(triisopropylsilyl)-1H-indole (2)

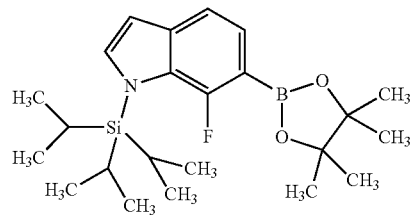 [SMILES: CC(C)[Si](C(C)C)(C(C)C)n1ccc2ccc(B3OC(C)(C)C(C)(C)O3)c(F)c21]

The title compound was prepared as in Preparation 50, Precursor Example 3 in U.S. Patent Application Publication No. 2014/0274695.

Example 3: Preparation of methyl 4-amino-3-chloro-5-fluoro-6-(7-fluoro-1H-indol-6-yl)picolinate (3)

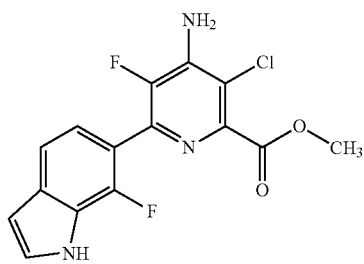 [SMILES: COC(=O)c1nc(-c2ccc3cc[nH]c3c2F)c(F)c(N)c1Cl]

The title compound can be prepared as described in Example 1 in U.S. Patent Application Publication No. 2014/0274695. Alternatively, it can be prepared as follows.

To a 3 liter (L), three-necked flask, fitted with magnetic stirring, condenser, internal temperature probe and nitrogen atmosphere, were added methyl 4-amino-3,6-dichloro-5-fluoropicolinate (prepared as in Fields et al., *Tetrahedron Letters* 2010, 51, 79-81; 75 grams (g), 314 millimoles (mmol)) and 7-fluoro-6-(4,4,5,5-tetramethyl-1,3,2-dioxaborolan-2-yl)-1-(triisopropylsilyl)-1H-indole (175 g, 377 mmol). Acetonitrile (CH$_3$CN; 1255 milliliters (mL)) and a 2 molar (M) solution of potassium phosphate (314 mL, 628 mmol) were added sequentially. The mixture was then evacuated and back-filled with nitrogen (3×) before bis-(triphenylphosphine)palladium dichloride (11.12 g, 15.69 mmol) was added. The flask was evacuated and back-filled (3×), and the mixture was heated at 65° C. After 3 hours (h), potassium fluoride (74.4 g, 1255 mmol) was added and heating was continued for an additional 16 h. The reaction mixture was allowed to cool to room temperature and was filtered through Celite. The phases were separated, and the solvent was removed under reduced pressure. The residue was triturated with hexane, and the solid was collected by filtration and washed with hexane. The resulting solid was treated with dichloromethane (CH$_2$Cl$_2$), filtered, rinsed with a small amount of CH$_2$Cl$_2$, and vacuum dried at 50° C. The title compound was isolated as an off-white solid (73.5 g, 69%).

Example 4: Preparation of 4-amino-3-chloro-5-fluoro-6-(7-fluoro-1H-indol-6-yl)picolinic acid (4)

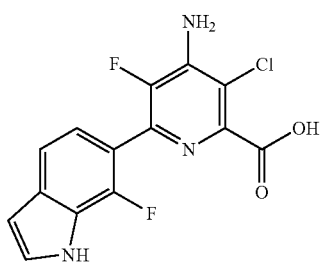 [SMILES: Nc1c(F)c(-c2ccc3cc[nH]c3c2F)nc(C(=O)O)c1Cl]

The title compound can be prepared as in Example 12 in U.S. Patent Application Publication No. 2014/0274695 or as follows.

Methyl 4-amino-3-chloro-5-fluoro-6-(7-fluoro-1H-indol-6-yl)picolinate (288 milligrams (mg), 0.853 mmol) was dissolved in tetrahydrofuran (THF; 2.0 mL), methanol (CH$_3$OH; 2.0 mL), and water (1.0 mL). Lithium hydroxide hydrate (100 mg, 2.383 mmol) was added. The reaction mixture was allowed to stir at room temperature overnight. The reaction mixture was concentrated to dryness. The resulting solid was diluted with water, and the suspension was made acidic (pH~3). The suspension was extracted with ethyl acetate (EtOAc; 3×). The combined organic extracts were washed with saturated aqueous sodium chloride (NaCl), dried over magnesium sulfate (MgSO$_4$), filtered and concentrated. The title compound was isolated as an off-white solid (256 mg, 93%).

Example 5: Preparation of prop-2-yn-1-yl 4-amino-3-chloro-5-fluoro-6-(7-fluoro-1H-indol-6-yl)picolinate (5)

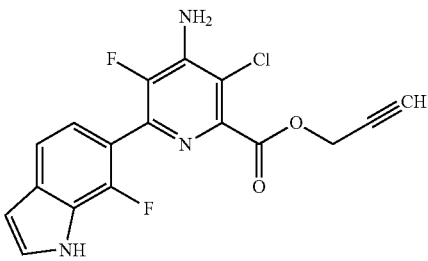 [SMILES: C#CCOC(=O)c1nc(-c2ccc3cc[nH]c3c2F)c(F)c(N)c1Cl]

A mixture of 4-amino-3-chloro-5-fluoro-6-(7-fluoro-1H-indol-6-yl)picolinic acid (1.5 g, 4.63 mmol), potassium carbonate (0.833 g, 6.02 mmol) and 3-bromopropyne (0.549 mL, 5.10 mmol) in N,N-dimethylformamide (DMF; 18.5 mL) was stirred at room temperature for 4 h. The reaction mixture was poured into a half-saturated aqueous solution of sodium bicarbonate (NaHCO$_3$) and extracted with EtOAc (2×). The combined organic extracts were dried over MgSO$_4$, filtered and concentrated. The residue was purified by automated flash column chromatography (silica gel, hexane/EtOAc gradient). To the resulting oil was added a minimum of CH$_2$Cl$_2$ to initiate the crystallization. Sonication was used to facilitate further crystallization. Hexane was then added to further precipitate the product. The solid was filtered, washed with hexane (2×) and dried in vacuo. The title compound was isolated as a white solid (1.33 g, 79%): mp 140-142° C.; $^1$H NMR (400 MHz, CDCl$_3$) δ 8.49 (s, 1H), 7.49 (dd, J=8.3, 0.7 Hz, 1H), 7.32-7.27 (m, 2H), 6.61 (td, J=3.3, 2.1 Hz, 1H), 4.97 (d, J=2.5 Hz, 2H), 4.91 (s, 2H), 2.53 (t, J=2.5 Hz, 1H); $^{19}$F NMR (376 MHz, CDCl$_3$) δ −135.47, −135.55, −137.23, −137.32; ESIMS m/z 362 ([M+H]$^+$).

The following compound was synthesized as in Example 5.

Cyanomethyl 4-amino-3-chloro-5-fluoro-6-(7-fluoro-1H-indol-6-yl)picolinate (6)

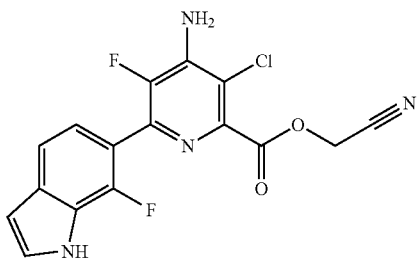 [SMILES: N#CCOC(=O)c1nc(-c2ccc3cc[nH]c3c2F)c(F)c(N)c1Cl]

The title compound was isolated as a white solid (730 mg, 65%): mp 139-140° C.; $^1$H NMR (300 MHz, DMSO-d$_6$) ☐ 11.83 (s, 1H), 7.52 (d, J=3.1 Hz, 1H), 7.47 (d, J=8.2 Hz, 1H), 7.13-7.03 (m, 3H), 6.59 (t, J=3.2 Hz, 1H), 5.29 (s, 2H); ESIMS m/z 363 ([M+H]$^+$).

Example 6: Evaluation of Postemergent Herbicidal Activity in the Greenhouse

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters (cm²). When required to ensure good germination and healthy plants, a fungicide treatment and/or other chemical or physical treatment was applied. The plants were grown for 7-36 days (d) in a greenhouse with an approximate 14 hour (h) photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

An aliquot of formulated Compound 5 (100 grams acid equivalent per liter (g ae/L); emusifiable concentrate (EC)), Compound 6 (100 g ae/L; EC) or Compound 7 (100 g ae/L; EC) was placed in a 25 mL glass vial and diluted in a volume of 1.25% (volume per volume (v/v)) aqueous Actirob B esterified rapeseed oil to obtain a stock solution. The concentrated stock solutions were diluted with an aqueous mixture of 1.25% v/v of aqueous Actirob B esterified rapeseed oil to provide the appropriate application rates. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters (m²) at a spray height of 18 inches (43 centimeters (cm)) above average plant canopy. Control plants were sprayed in the same manner with the solvent blank.

The treated plants and control plants were placed in a greenhouse as described above and watered by subirrigation to prevent washoff of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill.

Weed control was evaluated visually (as percent (%) visual control) at intervals indicated in the tables. The values reported are means. Means followed by the same letter in the tables do not significantly differ (P=0.5, Duncan's New MRT). The data are summarized in Table 1.

Example 7: Evaluation of Postemergence
Herbicidal in Field Trials in Canada

Field trials were established in Canada (in Ellerslie, Alberta; Nisku, Alberta and Hanley, Saskatchewan) to evaluate the efficacy of Compound 5, Compound 6, and Compound 7. Trials were designed as randomized complete blocks with four replicates. Trials were established in spring wheat with natural weed population with plot sizes of 2-3 meters (m) by 8-10 m (width×length). The crops were grown using normal cultural practices for fertilization, seeding, and maintenance to ensure good growth of the crop.

All herbicide treatments were applied post-emergence with applications made to the crops at BBCH (Phenological development stages of a plant) 14 to 22 growth stage. Herbicides were applied with backpack or bicycle sprayers using carbon dioxide ($CO_2$) as a propellant. The sprayers utilized flat fan air-induction spray nozzles calibrated to deliver a uniform spray pattern that provided thorough coverage of the foliage using a 100 L/ha spray volume. All treatments were applied with methylated seed oil (MSO) at 1.25% v/v. Phytotoxicity to the weeds was assessed visually at several intervals after application as percent overall control, compared to an untreated control plot. In general, four replicates were assessed for each treatment. All treatment results are an average of four replicates.

Herbicide Treatments

Compound 5, Compound 6 and Compound 7 were applied as emulsifiable concentrate (EC) formulations at 100 g ae/L EC, respectively.

The results are given in Table 2 through Table 4.

Example 8: Evaluation of Postemergence
Herbicidal in Field Trials in Spain and Germany Field trials were established in Spain (Banares and Granon) and Germany (Bielefeld) to evaluate the efficacy of Compound 5, Compound 6, and Compound 7. Trials were designed as randomized complete blocks with three to four replicates. Trials were established in winter wheat with natural weed population with plot sizes of 2-2.5 meters (m) by 6-8 m (width×length). The crops were grown using normal cultural practices for fertilization, seeding, and maintenance to ensure good growth of the crop.

All herbicide treatments were applied post-emergence with applications made to the crops at the BBCH 21 to 23 growth stage. Herbicides were applied with backpack or bicycle sprayers using air as a propellant. The sprayers utilized flat fan air-induction spray nozzles calibrated to deliver a uniform spray pattern that provided thorough coverage of the foliage using a 200 L/ha spray volume. All treatments were applied with methylated seed oil (MSO) at 1.25% v/v. Phytotoxicity to the weeds was assessed visually at several intervals after application as percent overall control, compared to an untreated control plot. In general, three to four replicates were assessed for each treatment. All treatment results are an average of three or four replicates.

Herbicide Treatments

Compound 5, Compound 6, and Compound 7 were applied as emulsifiable concentrate (EC) formulations at 100 g ae/L EC, respectively.

The results are given in Table 5 through Table 8.

The following abbreviations are used in Tables 1 to 8:

Compound 5=prop-2-yn-1-yl 4-amino-3-chloro-5-fluoro-6-(7-fluoro-1H-indol-6-yl)picolinate

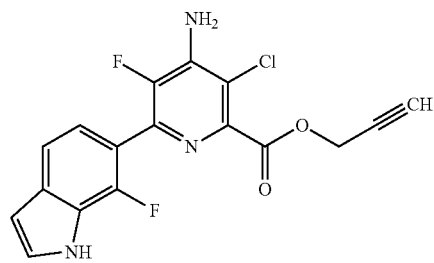 [SMILES: C#CCOC(=O)c1nc(-c2ccc3cc[nH]c3c2F)c(F)c(N)c1Cl]

Compound 6=cyanomethyl 4-amino-3-chloro-5-fluoro-6-(7-fluoro-1H-indol-6-yl)picolinate

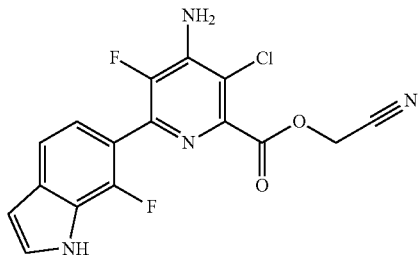 [SMILES: N#CCOC(=O)c1nc(-c2ccc3cc[nH]c3c2F)c(F)c(N)c1Cl]

Compound 7=benzyl 4-amino-3-chloro-5-fluoro-6-(7-fluoro-1H-indol-6-yl)picolinate

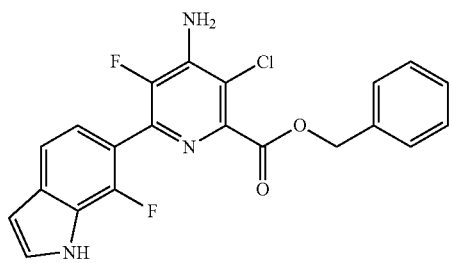 [SMILES: Nc1c(F)c(-c2ccc3cc[nH]c3c2F)nc(C(=O)OCc2ccccc2)c1Cl]

ANTAR=*Anthemis arvensis* (field chamomile)
CENCY=*Centaurea cyanus* (cornflower)
CHEAL=*Chenopodium album* L. (common lambsquarters)
CIRAR=*Cirsium arvense* (L.) Scop. (Canada thistle)
FUMOF=*Fumaria officinalis* (common fumitory)
KCHSC=*Kochia scoparia* (L.) Schrad. (*Kochia*)
MATCH=*Matricaria recutita* L. (wild chamomile)
MATIN=*Matricaria inodora* (scentless mayweed)
PAPRH=*Papaver rhoeas* L. (common poppy)
Res-PAPRH=*Papaver rhoeas* L. (common poppy) which is resistant to tribenuron and thifensulfuron (ALS—acetolactate synthase mode of action) and 2,4-D
POLCO=*Polygonum convolvulus* L. (wild buckwheat)
SINAR=*Sinapis arvensis* L. (wild mustard)
STEME=*Stellaria media* (L.) Vill. (common chickweed)
VERHE=*Veronica hederifolia* (ivyleaved speedwell)
VERSS=*Veronica* spp (speedwell)
g ae/ha=grams acid equivalent per hectare
LSD=least significant difference
DAAA=days after application A

TABLE 1

Percent (%) Visual Control of Key Weeds by Herbicidal Compounds under Greenhouse Conditions

| Compound | Rate (g ae/ha) | Percent (%) Visual Control 21-28 DAAA | | | | | |
|---|---|---|---|---|---|---|---|
| | | KCHSC | PAPRH | Res-PAPRH | SINAR | VERSS | ANTAR |
| 7 (benzyl ester) | 10 | 65 | 85 | 92.5 | 90 | 72.5 | 99.3 |
| 5 (propargyl ester) | 10 | 76.7 | 95 | 87.5 | 89 | 77.5 | 100 |
| 6 (cyanomethyl ester) | 10 | 73.3 | 100 | 95 | 90 | 86.3 | 100 |
| 7 | 20 | 73.3 | 100 | 92.5 | 94 | 67.5 | 99.3 |
| 5 | 20 | 82.7 | 100 | 100 | 96.7 | 80.8 | 83.3 |
| 6 | 20 | 84.3 | 100 | 100 | 96 | 86.5 | 98.3 |

| Compound | Rate (g ae/ha) | Percent (%) Visual Control 21-28 DAAA | | | | |
|---|---|---|---|---|---|---|
| | | CHEAL | CIRAR | MATCH | MATIN | POLCO |
| 7 | 10 | 92.5 | 30 | 57 | 100 | 97.5 |
| 5 | 10 | 97.5 | 56.7 | 54.2 | 100 | 100 |
| 6 | 10 | 100 | 50 | 57 | 98.3 | 98.3 |
| 7 | 20 | 95 | 46.7 | 50.5 | 100 | 98.8 |
| 5 | 20 | 100 | 58.3 | 68.9 | 100 | 100 |
| 6 | 20 | 100 | 58.3 | 64 | 100 | 100 |

TABLE 2

Percent (%) Visual Control of Key Weeds by Herbicidal Compounds under Field Conditions in Hanley, Saskatchewan, Canada (66 Days after Application A (66DAAA))

| Compound | Rate (g ae/ha) | Percent (%) Visual Control 66DAAA | | |
|---|---|---|---|---|
| | | KCHSC | CHEAL | POLCO |
| 7 | 10 | 45 | 95.5 | 46.3 |
| 6 | 10 | 62 | 95 | 47.5 |
| 7 | 20 | 72 | 98.5 | 63.3 |
| 6 | 20 | 81.5 | 98.3 | 68.8 |
| 7 | 40 | 78.8 | 98.8 | 70 |
| 6 | 40 | 92.5 | 99 | 85.8 |

TABLE 3

Percent (%) Visual Control of Key Weeds by Herbicidal Compounds under Field Conditions in Nisku, Alberta, Canada (28-51 Days after Application A (28-51DAAA))

| Compound | Rate (g ae/ha) | Percent (%) Visual Control | | |
|---|---|---|---|---|
| | | STEME 28DAAA | CHEAL 51DAAA | STEME 51DAAA |
| 7 | 10 | 76.7 | 98 | 76.3 |
| 6 | 10 | 99 | 98 | 87.5 |
| 5 | 10 | 88 | 98 | 88.3 |
| 7 | 20 | 76.7 | 98 | 80 |
| 6 | 20 | 96 | 98 | 87.8 |
| 5 | 20 | 96 | 96.8 | 92.5 |
| 7 | 40 | 99 | 98 | 85.8 |
| 6 | 40 | 99 | 98 | 94.5 |
| 5 | 40 | 99 | 97.3 | 93.8 |

TABLE 4

Percent (%) Visual Control of Key Weeds by Herbicidal Compounds under Field Conditions in Ellerslie, Alberta, Canada (51 Days after Application A (51DAAA))

| Compound | Rate (g ae/ha) | Percent (%) Visual Control | | |
|---|---|---|---|---|
| | | POLCO 51DAAA | CHEAL 51DAAA | STEME 51DAAA |
| 7 | 10 | 79 | 94.8 | 73.3 |
| 6 | 10 | 90.3 | 96.8 | 83.8 |
| 5 | 10 | 76.3 | 98 | 66.3 |
| 7 | 20 | 92.8 | 98 | 80.8 |
| 6 | 20 | 84.5 | 98 | 75.8 |
| 5 | 20 | 91 | 98 | 83.3 |
| 7 | 40 | 96.8 | 98 | 83.3 |
| 6 | 40 | 87 | 98 | 90 |

TABLE 5

Percent (%) Visual Control of Key Weeds by Herbicidal Compounds under Field Conditions in Granon, Spain (34-84 Days after Application A (34-84DAAA))

| Compound | Rate (g ae/ha) | Percent (%) Visual Control | |
|---|---|---|---|
| | | PAPRH 84DAAA | VERHE 34DAAA |
| 7 | 5 | 59.3 | 51.7 |
| 5 | 5 | 66.7 | 60 |
| 6 | 5 | 68.7 | 55 |
| 7 | 10 | 68.3 | 58.3 |
| 5 | 10 | 78.3 | 77 |
| 6 | 10 | 81 | 77.7 |
| 7 | 20 | 80.3 | 79.3 |
| 5 | 20 | 90.7 | 85 |
| 6 | 20 | 90 | 86 |

TABLE 6

Percent (%) Visual Control of Key Weeds by Herbicidal Compounds under Field Conditions in Banares, Spain (66-83 Days after Application A (66-83DAAA))

| Compound | Rate (g ae/ha) | Percent (%) Visual Control | | |
|---|---|---|---|---|
| | | PAPRH 66DAAA | VERHE 66DAAA | FUMOF 83DAAA |
| 7 | 5 | 53.3 | 50 | 26.7 |
| 5 | 5 | 57.7 | 60 | 41.7 |
| 6 | 5 | 60 | 60 | 41.7 |
| 7 | 10 | 62.7 | 56 | 45 |
| 5 | 10 | 70 | 77.7 | 65 |
| 6 | 10 | 75 | 81.7 | 69.3 |
| 7 | 20 | 75 | 70 | 58.3 |
| 5 | 20 | 90 | 91 | 93.3 |
| 6 | 20 | 91 | 91 | 96 |

TABLE 7

Percent (%) Visual Control of Key Weeds by Herbicidal Compounds under Field Conditions in Granon, Spain (48-68 Days after Application A (48-68DAAA))

| Compound | Rate (g ae/ha) | Percent (%) Visual Control | |
|---|---|---|---|
| | | PAPRH 68DAAA | SINAR 48DAAA |
| 7 | 5 | 45 | 73.3 |
| 5 | 5 | 58.3 | 85 |
| 6 | 5 | 55 | 82.7 |
| 7 | 10 | 60 | 80.7 |
| 5 | 10 | 72.7 | 94.8 |
| 6 | 10 | 69.3 | 95 |
| 7 | 20 | 74.3 | 89.3 |
| 5 | 20 | 79.3 | 95 |
| 6 | 20 | 85.3 | 95.2 |

TABLE 8

Percent (%) Visual Control of Key Weeds by Herbicidal Compounds under Field Conditions in Bielefed, Germany (85 Days after Application A (85DAAA))

| Compound | Rate (g ae/ha) | Percent (%) Visual Control | |
|---|---|---|---|
| | | PAPRH 85DAAA | CENCY 85DAAA |
| 7 | 5 | 66.3 | 32.5 |
| 5 | 5 | 92.5 | 65 |
| 6 | 5 | 94.5 | 60 |
| 7 | 10 | 78.8 | 53.8 |
| 5 | 10 | 97.3 | 87.5 |
| 6 | 10 | 97.3 | 92.5 |
| 7 | 20 | 80 | 62.5 |
| 5 | 20 | 98.8 | 95 |
| 6 | 20 | 99.8 | 97 |

As can be seen from the aforementioned results, the present compounds of Formula (I) have herbicidal activity. As can also be seen from the abovementioned results, Compound 5 and Compound 6 demonstrated superior herbicidal activity over Compound 7. These new chemical herbicides offer a broader spectrum of weed control, higher activity against weeds, and provide a way to address the management of weeds that developed resistance with respect to herbicides traditionally used to control them.

While this disclosure has been described as having exemplary aspects or embodiments, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

The benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described.

What is claimed is:
1. A compound of Formula (I):

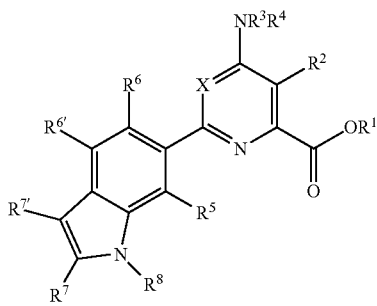

(I)

wherein
X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkoxy, $C_1$-$C_3$ alkylthio, or $C_1$-$C_3$ haloalkylthio;
$R^1$ is $C_3$-$C_{12}$ alkynyl or $C_1$-$C_3$ alkyl substituted with CN;
$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$— $SiR^{19}R^{20}R^{21}$, wherein $R^{17}$ is hydrogen, F, or Cl;

$R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;
$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;
$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;
$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;
$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;
$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_6$ alkylcarbonyl, $C_1$-$C_6$ cycloalkylcarbonyl, $C_1$-$C_6$ haloalkylcarbonyl, $C_1$-$C_6$ alkoxycarbonyl, $C_1$-$C_6$ haloalkoxycarbonyl, arylcarbonyl, heteroarylcarbonyl, $C_1$-$C_6$ alkylcarbamyl, $C_1$-$C_6$ alkylthio, $C_1$-$C_6$ alkylsulfonyl, $C_1$-$C_6$ haloalkylsulfonyl, arylsulfonyl, $C_1$-$C_6$ trialkylsilyl, amino, $C_1$-$C_4$ alkylamino, cyano, or phenyl;
or an N-oxide or agriculturally acceptable salt thereof.

2. The compound of claim 1, wherein
X is N, CH, CF, CCl, or CBr;
$R^1$ is $C_3$-$C_{12}$ alkynyl or $C_1$-$C_3$ alkyl substituted with CN;
$R^2$ is chlorine;
$R^3$ and $R^4$ are hydrogen;
$R^5$ is hydrogen, halogen, OH, amino, CN, $C_1$-$C_3$ alkyl, $C_1$-$C_3$ alkoxy, $C_1$-$C_3$ alkylamino, or cyclopropyl;
$R^6$ and $R^{6'}$ are independently hydrogen, halogen, OH, $NH_2$, CN, $C_1$-$C_3$ alkyl, $C_1$-$C_3$ alkoxy, cyclopropyl, or vinyl;
$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and
$R^8$ is hydrogen, $C_1$-$C_3$ alkyl, phenyl, or $C_1$-$C_3$ alkylcarbonyl;
or an N-oxide or agriculturally acceptable salt thereof.

3. The compound of claim 1, wherein
X is CH, CF, or N;
$R^1$ is $C_3$-$C_{12}$ alkynyl or $C_1$-$C_3$ alkyl substituted with CN;
$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

R$^3$ and R$^4$ are hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or C$_1$-C$_6$ alkylamino;

R$^5$ is hydrogen, halogen, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, or C$_2$-C$_4$ haloalkylamino;

R$^6$ and R$^{6'}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, CN, or NO$_2$;

R$^7$ and R$^{7'}$ are independently hydrogen, halogen, C$_1$-C$_4$ alkyl, C$_1$-C$_4$ haloalkyl, C$_1$-C$_3$ alkoxy, C$_1$-C$_3$ haloalkoxy, C$_1$-C$_3$ alkylthio, cyclopropyl, amino or C$_1$-C$_4$ alkylamino;

R$^8$ is hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_6$ alkylcarbonyl, C$_1$-C$_6$ cycloalkylcarbonyl, C$_1$-C$_6$ haloalkylcarbonyl, C$_1$-C$_6$ alkoxycarbonyl, C$_1$-C$_6$ haloalkoxycarbonyl, arylcarbonyl, heteroarylcarbonyl, C$_1$-C$_6$ alkylcarbamyl, C$_1$-C$_6$ alkylthio, C$_1$-C$_6$ alkylsulfonyl, C$_1$-C$_6$ haloalkylsulfonyl, arylsulfonyl, C$_1$-C$_6$ trialkylsilyl, amino, C$_1$-C$_4$ alkylamino, cyano, or phenyl.

4. The compound of claim 3, wherein: R$^2$ is halogen, C$_2$-C$_4$ alkenyl, C$_2$-C$_4$ haloalkenyl, or C$_1$-C$_4$ alkoxy.

5. The compound of claim 4, wherein R$^2$ is Cl, methoxy, vinyl, or 1-propenyl.

6. The compound of claim 3, wherein R$^3$ and R$^4$ are hydrogen.

7. The compound of claim 3, wherein R$^5$ is hydrogen or F.

8. The compound of claim 7, wherein R$^5$ is F.

9. The compound of claim 3, wherein R$^6$ is hydrogen or F.

10. The compound of claim 3, wherein R$^6$ and R$^{6'}$ are hydrogen.

11. The compound of claim 3, wherein R$^{6'}$ is hydrogen.

12. The compound of claim 3, wherein:
R$^2$ is halogen, C$_2$-C$_4$-alkenyl, C$_2$-C$_4$ haloalkenyl, or C$_1$-C$_4$ alkoxy;
R$^5$ is hydrogen or F;
R$^6$ is hydrogen or F;
R$^{6'}$ is hydrogen; and
R$^7$ and R$^{7'}$ are independently hydrogen or halogen.

13. The compound of claim 12, wherein R$^2$ is chlorine, methoxy, vinyl, or 1-propenyl.

14. The compound of claim 12, wherein R$^3$ and R$^4$ are hydrogen.

15. The compound of claim 13, wherein R$^3$ and R$^4$ are hydrogen.

16. The compound of claim 12, wherein X is CF.

17. The compound of claim 13, wherein X is CF.

18. The compound of claim 14, wherein X is CF.

19. The compound of claim 15, wherein X is CF.

20. The compound of claim 3, wherein:
R$^2$ is chlorine, methoxy, vinyl, or 1-propenyl; and
R$^3$ and R$^4$ are hydrogen.

21. The compound of claim 3, wherein:
R$^2$ is chlorine, methoxy, vinyl, or 1-propenyl;
R$^3$ and R$^4$ are hydrogen; and
X is CF.

22. The compound of claim 21, wherein the compound is prop-2-yn-1-yl 4-amino-3-chloro-5-fluoro-6-(7-fluoro-1H-indol-6-yl) picolinate.

23. The compound of claim 21, wherein the compound is cyanomethyl 4-amino-3-chloro-5-fluoro-6-(7-fluoro-1H-indol-6-yl) picolinate.

24. A herbicidal composition comprising the compound of claim 1 and an agriculturally acceptable adjuvant or carrier.

25. The composition of claim 24, further comprising at least one additional herbicidal compound.

26. The composition of claim 24, further comprising a safener.

27. A method for controlling undesirable vegetation comprising:
providing the compound of claim 1; and
applying the compound to an undesirable vegetation or a locus thereof.

28. A method for controlling undesirable vegetation comprising:
providing the composition of claim 25; and
applying the composition to an undesirable vegetation or a locus thereof.

* * * * *